(12) United States Patent
Roitman et al.

(10) Patent No.: US 7,005,268 B2
(45) Date of Patent: Feb. 28, 2006

(54) DETECTION OF BIOPOLYMERS UTILIZING PHOTO-INITIATED CHARGE SEPARATION

(75) Inventors: Daniel B. Roitman, Menlo Park, CA (US); Calvin B. Ward, Castro Valley, CA (US); Seiji Inaoka, Campbell, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 584 days.

(21) Appl. No.: 10/098,091

(22) Filed: Mar. 13, 2002

(65) Prior Publication Data
US 2003/0175718 A1   Sep. 18, 2003

(51) Int. Cl.
*G01N 33/53* (2006.01)

(52) U.S. Cl. .............. 435/7.1; 436/518; 436/524; 436/525; 422/82.01; 422/68.1; 204/194; 204/400; 204/403.1; 204/230.7

(58) Field of Classification Search .............. 435/4, 435/5, 6, 287.1, 287.2, 525, 7.1; 422/50, 422/68.1, 82.01; 436/518, 524; 204/193, 204/400, 403.01, 416, 403.13, 229.1, 229.8, 204/230.1, 230.7, 194
See application file for complete search history.

(56) References Cited

U.S. PATENT DOCUMENTS

| | | | | |
|---|---|---|---|---|
| 4,963,815 | A * | 10/1990 | Hafeman | 205/777.5 |
| 5,712,461 | A * | 1/1998 | Zhang et al. | 204/157.15 |
| 5,770,369 | A * | 6/1998 | Meade et al. | 435/6 |
| 5,990,479 | A * | 11/1999 | Weiss et al. | 250/307 |
| 6,264,825 | B1 * | 7/2001 | Blackburn et al. | 205/777.5 |
| 6,265,341 | B1 * | 7/2001 | Komatsu et al. | 502/326 |
| 6,293,310 | B1 * | 9/2001 | Redemann et al. | 137/884 |
| 6,294,245 | B1 * | 9/2001 | Roitman et al. | 428/212 |
| 6,319,670 | B1 * | 11/2001 | Sigal et al. | 435/6 |
| 6,407,330 | B1 * | 6/2002 | Lindsey et al. | 136/263 |
| 6,548,311 | B1 * | 4/2003 | Knoll | 436/524 |
| 6,664,071 | B1 * | 12/2003 | Windhab et al. | 435/7.94 |
| 6,677,606 | B1 * | 1/2004 | Rajh et al. | 257/40 |
| 2003/0143581 | A1 * | 7/2003 | Franzen et al. | 435/6 |

OTHER PUBLICATIONS

Herrmann et al. Characterization and photocatalytic activity in aqueous medium of TiO2 and Ag-TiO2 coatings on quartz. Nov. 1997. Applied Catalysis B: Environmental. vol. 13, pp. 219-228.*

Leytner et al. Evaluation of the energetics of electron trap states at the nanocrystalline titanium dioxide/aqueous solution interface via time-resolved photoacoustic spectroscopy. Nov. 2000. Chemical Physics Letters. vol. 330, pp. 231-236.*

* cited by examiner

*Primary Examiner*—Long V. Le
*Assistant Examiner*—Melanie J. Yu

(57) ABSTRACT

A method for detecting the presence of target molecules bound to a working electrode in a first location. The first location is coated with a detection solution containing labeling molecules that include a first charge-separation moiety attached to a first molecule that binds to the target molecule. The first charge-separation moiety includes a material that generates hole-electron pairs in response to being illuminated by light in a first band of wavelengths. After removing any unbound labeling, the working electrode is immersed in a solution containing a compound that is oxidized by the generated holes. The first location is then selectively illuminated with light in the first band; and the change in the current and/or potential is measured between the working electrode and a reference electrode in contact with the solution. The first charge-separation moiety is preferably constructed from particles of a semiconducting material such as $TiO_2$.

10 Claims, 3 Drawing Sheets

US 7,005,268 B2

DETECTION OF BIOPOLYMERS UTILIZING PHOTO-INITIATED CHARGE SEPARATION

FIELD OF THE INVENTION

The present invention relates to biochemical assays, and more particularly, to a method for detecting the presence of a particular molecule on a substrate.

BACKGROUND OF THE INVENTION

Tests based on the binding of one biomolecule to another are well known. For example, the presence of a particular nucleic acid sequence in a solution can be ascertained by detecting the binding of the nucleic acid to a substrate having an immobilized nucleic acid of the complementary sequence. Tests based on such hybridized binding are particularly attractive in that they allow one to test an unknown sample against a large number of possible matching candidates.

In many test systems such as nucleic acid testing systems, the presence of a bound target molecule requires a very high degree of sensitivity, since the amount of material that is bound to the immobilized "probes" is small. Prior art systems typically rely on special fluorescent labels on the targets or on intercalation dyes that selectively bind to double stranded nucleic acids. Both of these methods require the use of very sensitive fluorescence scanners that represent a high capital investment.

In addition to high sensitivity, assays that allow the detection of multiple dyes are particularly useful. The special fluorescent labels mentioned above can, in principle, be formulated to have different fluorescent bands to allow the measurement of several target species at a time. However, the cost of creating a large number of such dyes with fluorescent bands that are easily distinguished from one another is prohibitive.

Broadly, it is the object of the present invention to provide an improved binding assay that can provide the required sensitivity without the need for expensive fluorescence scanners.

These and other objects of the present invention will become apparent to those skilled in the art from the following detailed description of the invention and the accompanying drawings.

SUMMARY OF THE INVENTION

The present invention is a method for detecting the presence of target molecules bound to a working electrode in a first location. The first location is coated with a detection solution containing labeling molecules that include a first charge-separation moiety attached to a first molecule that binds to the target molecule. The first charge-separation moiety includes a material that generates hole-electron pairs in response to being illuminated by light in a first band of wavelengths. After removing any unbound labeling molecules from the working electrode, the working electrode is immersed in a solution containing a compound that is oxidized by the generated holes. The first location is then selectively illuminated with light in the first band; and the change in the current and/or potential is measured between the working electrode and a reference electrode in contact with the solution. The first charge-separation is preferably constructed from particles of a semiconducting material such as $TiO_2$. The detection solution may also include a second charge-separation moiety attached to a second molecule that binds to the target molecule at a second location on the target molecule. The second charge-separation moiety includes a material that generates hole-electron pairs in response to being illuminated by light in a second band of wavelengths, the second band of wavelengths being different from the first band of wavelengths. By performing measurements using two different illumination bands, different target molecules can be detected.

DETAILED DESCRIPTION OF THE INVENTION

Figure 1:
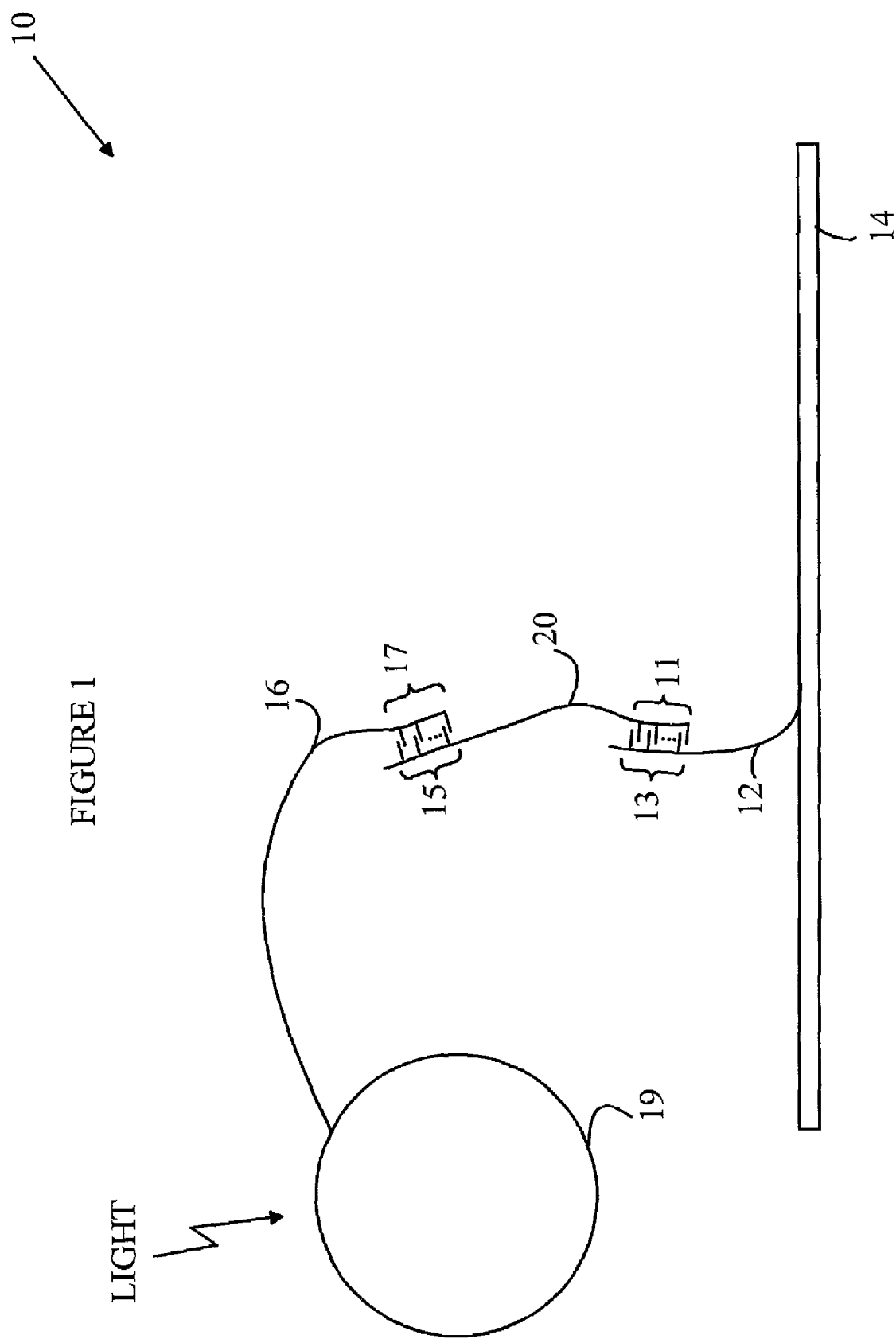
FIG. 1 is a schematic drawing of a portion of an assay plate 10 based on the complementary binding of nucleic acids.

The manner in which the present invention provides its advantages can be more easily understood with reference to FIG. 1, which is a schematic drawing of a portion of an assay plate 10 based on the complementary binding of nucleic acids. Assay plate 10 is used to detect target molecules 20 having two specific nucleotide sequences. A probe molecule 12 having the first sequence 13 is immobilized on a substrate 14. The target nucleic acid sequence 11 binds to probe 12 because it has the complementary sequence to sequence 13 on the probe. The target molecule also has a second nucleotide sequence 15 that binds to a labeling molecule 16 according to the present invention. The labeling molecule has a nucleotide sequence 17 that is complementary to sequence 15. In addition, the labeling molecule has a photo-inducible charge-separation moiety 19.

Charge-separation moiety 19 is capable of transforming light, or other electromagnetic radiation, into an electron-hole pair when a light source having sufficient energy in a predetermined wavelength band to excite moiety 19 is provided. In the present invention, the hole is used to oxidize a nearby molecule. The oxidizable molecule can be in solution or attached to the substrate. In addition, a reducible agent is provided to absorb the photo-electron.

The use of a charge separation moiety such as $TiO_2$ to oxidize an organic compound in the presence of light is known to the art, and hence, will not be discussed in detail here. For example, the photocatalysis of a number of organic compounds on $TiO_2$ particles is discussed in detail in Photocatalytic Purification and Treatment of Water and Air, Edited by D. F. Ollis and H. Al-Ekabi, Elfevibr, Amsterdam, 1993. The reader is specifically directed to the article entitled "$TiO_2$ Photocatalysis for the Destruction of Organics and Reduction of Heavy Metals, by Tom Mrpraire, et al. at p 353 in this book.

The amount of bound moiety 19 can be determined by measuring the rate of conversion of the reducible compound under conditions in which the oxidizable and reducible compounds are present in sufficient quantity to assure that the rate of reaction is determined by the amount of bound photocatalysis. The rate of reaction can be determined by the amount of charge that is transferred to the reducible agent in a fixed period of time. For example, silver cation can be used as the reducible agent. In this case, the amount of metallic silver formed is a measure of the amount of moiety 19 that is bound to the assay substrate. The amount of silver that is reduced can be amplified using conventional techniques to form a spot that can be detected optically after the assay is developed.

Schemes based on production of metallic silver can provide a means for assaying for a number of different target molecules by providing different probe molecules at different locations on an assay plate. The amount of each target molecule is related to the amount of $TiO_2$ that is bound at the corresponding spot. The amount of $TiO_2$ is, in turn, measured by measuring the amount of silver that is deposited at each spot. This measurement requires that the final assay plate be scanned to measure the amount of silver.

Such schemes have a number of limitations. First, the assay must be developed to provide the required sensitivity. The development phase increases the cost and time required to provide the result. Second, assays in which different labeling molecules are used in the same assay are difficult to construct.

The present invention is based on the observation that the transfer of charge to the reducible agent can be measured by providing a working electrode of an electrochemical instrument as the final electron acceptor. In this case, the current through the working electrode when moiety 19 is exposed to light of the appropriate wavelength provides a measurement of the amount of bound moiety 19. The working electrode may be incorporated in substrate 14.

Substrate 14 can be constructed from a wide range of materials. For example, substrates can be constructed from indium tin oxide or silicon. Methods for attaching DNA and RNA probes to a conductive substrate via a polymeric coating on the conductive member in a manner suitable for forming a working electrode are known to the art, and hence, will not be discussed in detail here. Exemplary attachment methods are taught in U.S. Pat. No. 5,968,745 to Thorp, et al, which is hereby incorporated by reference.

The preferred charge separation moiety is $TiO_2$ particles. Particles up to 100 nm may be utilized. The large size of these particles increases the detection sensitivity. In addition, particles constructed from oxides of tin and tungsten can also be utilized.

The wavelength of light that excites the particles can be altered by including a sensitization dye on the surface of the particles. Such dyes are known in the solar cell arts, and hence will not be discussed in detail here. The reader is directed to "The Electrochemistry of Dye Sensitized Solar Cells, their Sensitizers, and their Redox Shuttles, Ph.D. Thesis by George G. WolfBauer, Monash University, Australia, 1999. The activation wavelength of the particles can also be altered by doping the material used to construct the particles. $TiO_2$ Particles doped with metals such as Pt, Ir, C, Co, Tb, Mn, and Cr are known to have altered activation spectra. Doping $TiO_2$ in bulk as opposed to the surface of the particles creates additional intermediate states in the material, and hence, alters the spectrum in a manner different from the alterations obtained with surface dye sensitization. The activation spectra of particles based on oxides of tin or tungsten can also be altered by such doping. The reader is directed to "Combinatorial Discovery of New Photocatalysis for Water Purification with Visible Light", by C. Lettmann, et al., in Angew. Chem. intl. ed, 2001, v40, p. 3160 for a more detailed discussion of such doping.

Particles with different activation spectra can be used to assay different bound molecules. In such assays, the response of the assay plate when scanned with different light wavelengths can be used to determine the concentration of each bound particle.

Figure 2:
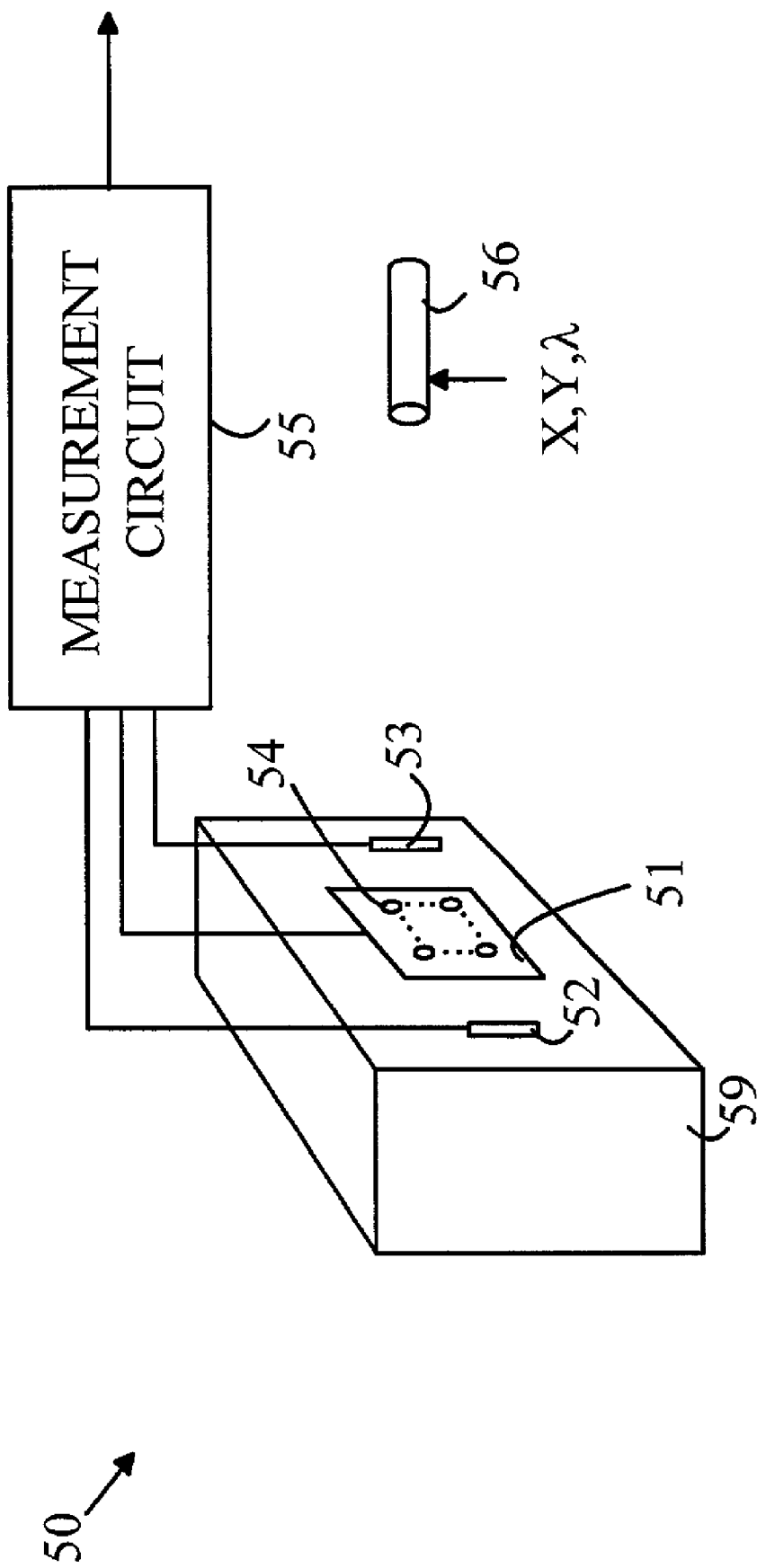
FIG. 2 is a schematic drawing of a measurement apparatus 50 according to the present invention.

Refer now to FIG. 2, which is a schematic drawing of a measurement apparatus 50 according to the present invention. Apparatus 50 is based on an assay plate 51 of the type shown in FIG. 2. Assay plate 51 has a plurality of separate assay regions 54. Each assay region has a different probe molecule attached thereto. A light source 56 selectively illuminates the spots in response to an input signal specifying a location on assay plate 51 and a wavelength.

As noted above, assay plate 51 forms the working electrode of an electrochemical instrument comprising assay plate 51, a reference electrode 52, and a counter electrode 53. In the preferred embodiment of the present invention, measurement circuit 55 measures the current flowing between the counter electrode and the working electrode while the potential between the working electrode and reference electrode is maintained at a constant value. A saturated calomel electrode and a platinum flag electrode can be utilized for the reference and counter electrodes, respectively. However, embodiments in which the counter electrode is omitted can also be practiced. In such embodiments, the reference electrode also serves as the counter electrode. The reference electrode of the electrochemical cell provides the reducible component of the system.

As noted above, the present invention requires an oxidizable substance in the electrochemical cell 59. Hydroquinone at a concentration of about 0.1 molar can be utilized for this component. However, any of a large number of organic compounds can also be utilized as evidenced by the fact that photocatalysis of numerous organic compounds on $TiO_2$ has been demonstrated. The Photochemical Technology article listed above provides numerous examples of such chemicals, and hence, these chemicals will not be listed in detail here.

The above-described embodiments of the present invention require that the $TiO_2$ particles be coupled to a nucleic acid strand. This can be accomplished by a number of techniques that are known to the art, and hence will not be discussed in detail here. For the purposes of this discussion, two techniques will be outlined. First, a metal oxide ($M_yO_x$) can be modified by organosilane compounds resulting in the formation of M-O—Si bonds. The organosilanes contain suitable organic functional groups capable of undergoing chemical reactions with linkers or biomolecules (see Conjugate Techniques by G. T. Hermanson, Academic Press, 1996). For example, the reaction between an oxide surface and trimethoxyaminopropyl silane results in the attachment of primary amine functional groups to the surface. These functional groups are then used to attach the molecules of interest to the surface of the metal oxide surface.

A second method for modification of the oxide surface is to form a complex between the oxide and functional groups that form a tight association with the surface of the oxide without becoming covalently bonded to the metal oxide. For example, dopamine, isocyanate ions, and alanine form tight complexes with $TiO_2$. In the case of $TiO_2$ these moieties can also play a role in assisting transfer of the holes from the $TiO_2$ particles to the surrounding solution. These sensitizing molecules can be conjugated directly to biomolecules, or they can be functionalized and used as conjugation linkers for biomolecules, ligands, etc.

Figure 3:
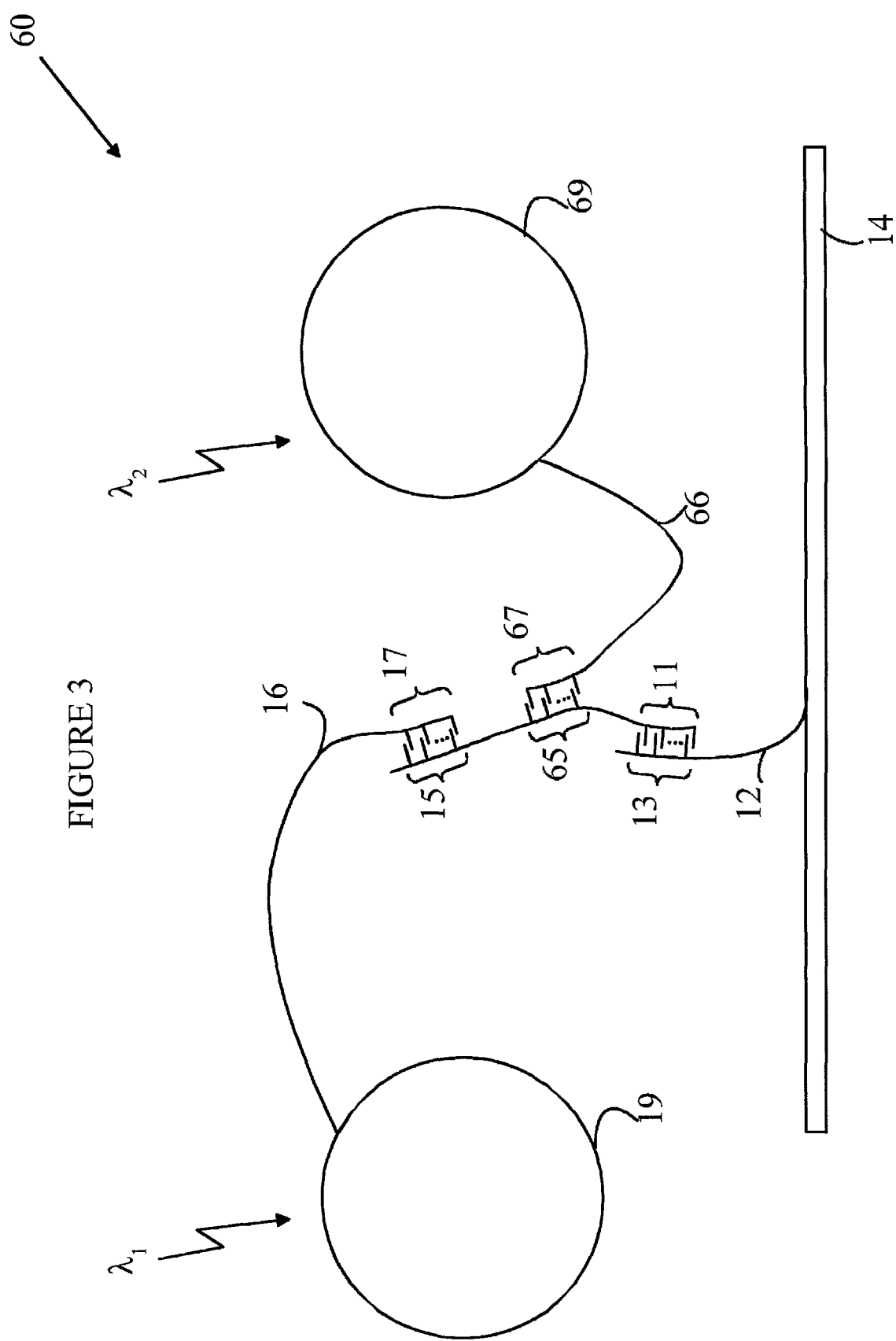
FIG. 3 illustrates a detection system in which two different labeling molecules are utilized.

As noted above, it would be advantageous to be able to utilize labeling molecules having different activation bands. The above-described embodiments have utilized a single species of labeling molecule. These embodiments cannot easily distinguish between labeling molecules that are properly bound to the immobilized target and molecules that bind non-specifically to the surface on which the target is immobilized. By utilizing labeling molecules with different activation bands and binding sites, such non-specific binding can be detected. Refer now to FIG. 3, which illustrates a detection system 60 in which two different labeling molecules are utilized. To simplify the following discussion, the elements shown in FIG. 3 that serve the same function as elements shown in FIG. 1 have been given the same numeric designations. The first labeling molecule 16 is the same as that described above with respect to FIG. 1. A second labeling molecule 66 having a sequence 67 that is complementary to the target species at a location 65 is also used. Labeling molecule 66 binds a second charge-separation moiety 69, which is activated by light in a different band from that of charge-separation moiety 19.

In an assay according to this embodiment of the present invention, the assay plate is first immersed in a solution containing the target molecules. After removing any unbound target molecules, a detection solution containing the two different labeling molecules is used to coat the assay plate. Any unbound labeling molecules are removed by washing. The assay plate is then placed in the apparatus shown in FIG. 2 and the current generated by each spot at two different wavelengths is measured. If either of the two labeling molecules is non-specifically bound to other structures in the assay plate, the ratio of the observed currents at the two different wavelengths will be different from that predicted for specific attachment of the labeling molecules.

The above-described embodiments of the present invention have utilized assays in which the binding of nucleic acids is detected by labeling one of the nucleic acid strands with the metal oxide particles of the present invention. However, the present invention may also be utilized in assays based on the binding of other biomolecules such as antibodies and antigens, enzyme substrate binding, and the like. In essence, the charge separation moieties of the present invention can be used in place of the fluorescent dyes normally utilized by such assays.

The above-described embodiments of the present invention depend on the hole generated within the charge separation moiety escaping from the metal oxide particle. Holes that recombine with electrons within the particles do not produce a detectable electric signal. The fraction of holes generated in the particles that escape the particles can be increased by adding electron scavengers to the solution. The scavengers remove the electrons from the particles before the electrons can recombine with the holes. In particular, copper ions, ferric iron ions and methyl-viologen dye cation can be added to the solution to improve the electrical signal from the illumination of the particles.

Various modifications to the present invention will become apparent to those skilled in the art from the foregoing description and accompanying drawings. Accordingly, the present invention is to be limited solely by the scope of the following claims.

What is claimed is:

1. A method for detecting the presence of target molecules bound to a working electrode in a first location, said method comprising the steps of:
   coating said first location with a detection solution containing labeling molecules comprising a first charge-separation moiety attached to a first molecule that binds to said target molecule after said target molecules having been bound to said working electrode in said first location, said first charge-separation moiety comprising a semiconducting material that generates hole-electron pairs in response to being illuminated by light in a first band of wavelengths;
   removing any unbound labeling molecules from said working electrode;
   immersing said working electrode in a solution containing a compound that is oxidized by said generated holes;
   selectively illuminating said first location with light in said first band while said working electrode is immersed in said solution; and
   measuring a change in an electrical quantity between said working electrode and a reference electrode in contact with said solution to detect labeling molecules that are bound to said target molecules.

2. The method of claim 1 wherein the first molecule of said labeling molecules comprise nucleic acids.

3. The method of claim 1 wherein the first molecule of said labeling molecules comprise antibodies.

4. The method of claim 1 wherein the first molecule of said labeling molecules comprise enzymes.

5. The method of claim 1 wherein said semiconducting material comprises $TiO_2$.

6. The method of claim 1 wherein said electrical quantity is a current flowing between said working electrode and said reference electrode.

7. The method of claim 6 wherein said electrical quantity is a potential difference between said working electrode and said reference electrode.

8. The method of claim 1 wherein said detection solution further comprises a second charge-separation moiety attached to a second molecule that binds to said target molecule, said second charge-separation moiety comprising a material that generates hole-electron pairs in response to being illuminated by light in a second band of wavelengths, said second band of wavelengths being different from said first band of wavelengths.

9. The method of claim 8 wherein said second charge-separation moiety comprises $TiO_2$.

10. The method of claim 8 further comprising the steps of:
    illuminating said first location with light in said second band; and
    measuring the change in an electrical quantity between said working electrode and a reference electrode in contact with said solution.

* * * * *